Figure 1:
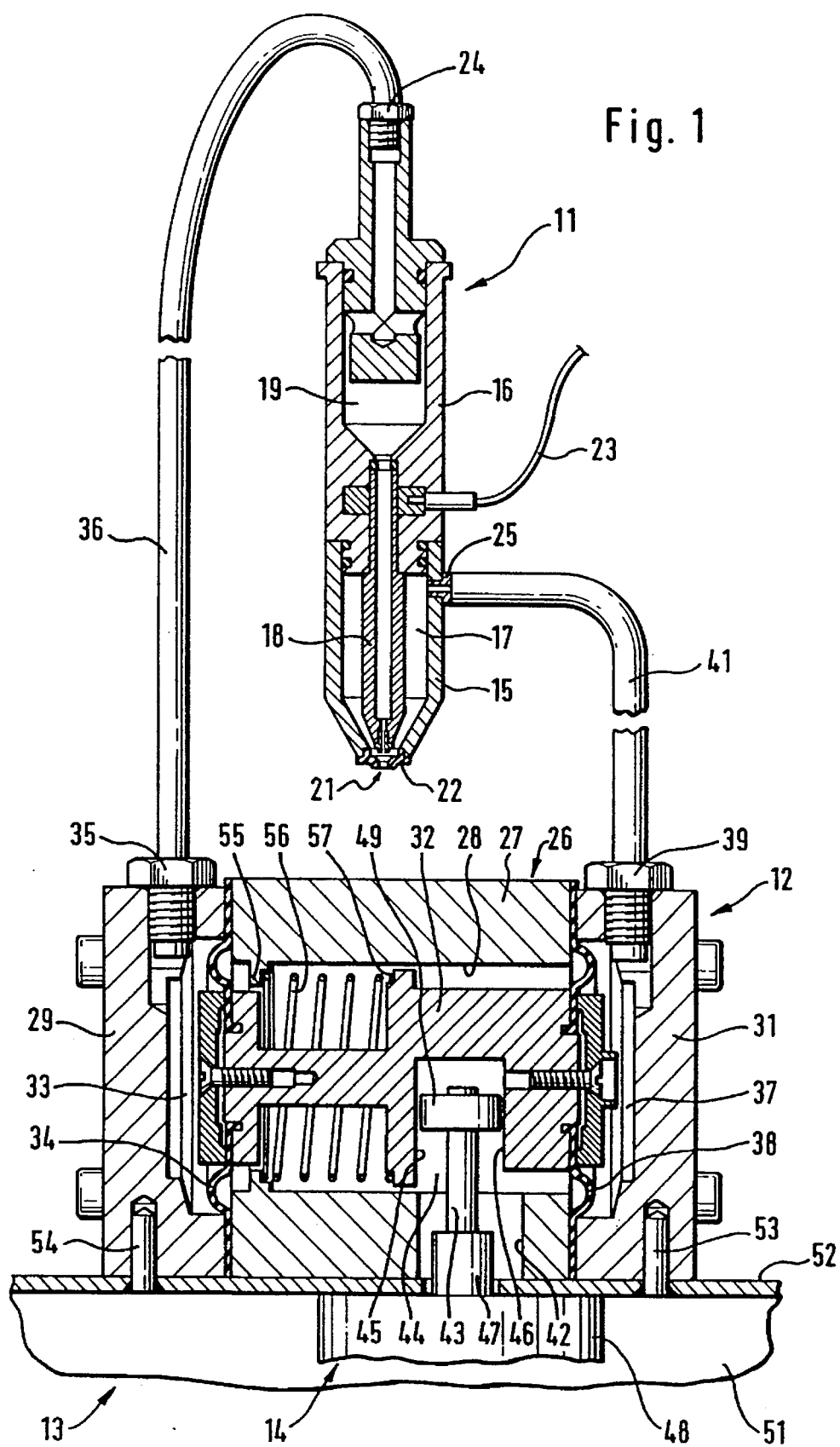

United States Patent [19]

Fischer

[11] Patent Number: 5,498,957
[45] Date of Patent: Mar. 12, 1996

[54] APPLIANCE AND METHOD FOR THE COULOMETRIC MEASUREMENT OF THE THICKNESS OF METALLIC COATINGS

[76] Inventor: Helmut Fischer, Instriestrasse 21, 71069 Sindelfingen, Germany

[21] Appl. No.: 333,953

[22] Filed: Nov. 3, 1994

[30] Foreign Application Priority Data

Nov. 10, 1993 [DE] Germany .......................... 43 38 211.8

[51] Int. Cl.⁶ ................................................ G01R 27/02
[52] U.S. Cl. ...................................... 324/158.1; 324/719
[58] Field of Search .................................. 324/62, 60, 92, 324/158.1; 339/118 R

[56] References Cited

U.S. PATENT DOCUMENTS

Re. 32,024   11/1985   Greig ................................... 324/158 F
3,794,912    2/1974    Severin et al. ............................ 324/62

FOREIGN PATENT DOCUMENTS 3831399   9/1991   Germany .

*Primary Examiner*—Kenneth A. Wieder
*Assistant Examiner*—Barry C. Bowser

[57] ABSTRACT

An appliance for the coulometric measurement of the thickness of metallic coatings comprises a measuring probe (11) and a reversing pump device (12) with the aid of which the electrolyte fluid can be conveyed from a reservoir chamber (19) of the measuring probe (11) into the measuring chamber (17) thereof and back again. The measuring probe (11), together with the reversing pump device (12), forms a functional unit which, as a whole, can be coupled to the support device (13) and be uncoupled therefrom again. In the process, the pump drive (14) remains on the support device (13). A change of measuring probes, charged so as to be ready for service, is thus possible simply and quickly, which permits rapid measurement of a plurality of successive coatings on one measurement object to be performed. The functional unit of measuring probe and reversing pump device prevents unintentional outflow of the electrolyte fluid. It is further ensured, by means of a compression spring (56), that the electrolyte is automatically drawn into the reservoir chamber (19) if inadvertent separation from the pump drive (14) should occur.

7 Claims, 1 Drawing Sheet

APPLIANCE AND METHOD FOR THE COULOMETRIC MEASUREMENT OF THE THICKNESS OF METALLIC COATINGS

The invention relates to an appliance according to the precharacterizing clause of claim 1.

An appliance of the same generic type is disclosed in DE 38 31 399 A1. While a support device is not mentioned, it can be assumed to be present, as can a pump drive. In the known appliance, the second hose connection is likewise connected, via an air line, to a fourth hose connection which opens into a second pump chamber whose volume is varied by a common piston, in antiphase to that of the first pump chamber. As a result, the system is closed, apart from the outlet orifice which, however, during the measurement is situated on the measurement object. Immediately upstream of the measuring chamber and the reservoir chamber, a so-called reversing chamber is interposed in each case which basically only acts as a volume expansion means. The electrolyte is distributed over the four chambers, depending on the piston position, the piston being moved back and forth (reversed) a number of times during the measurement, which causes a constant electrolyte exchange to take place at the measuring point in the vicinity of the outlet orifice. In order to facilitate initial charging, provision is made for one of the reversing chambers to be used as an interchangeable, precharged magazine, from which it follows that the other components, in particular the reversing pump device, are fixedly installed on the support device or on the instrument housing. Since, during operation, the electrolyte is at all times distributed over all the chambers, a changeover to a different electrolyte is only possible after laborious emptying and recharging of the system. Multiple layers of different coatings, which each require a different electrolyte, can therefore be measured only in a very laborious and time-consuming manner.

The object of the invention is to provide an appliance of the type as defined in the preamble, which permits time-saving measurement of multiple layers on one measurement object, and to specify a method for time-saving multiple-layer measurement.

This object is achieved with respect to the appliance by the characterizing features of claim 1.

As a result of the measuring probe remaining linked to the reversing pump device as a functional unit when the measuring probe is removed from the support device, inadvertent outflow of the electrolyte fluid can be prevented or at least hindered. Thus it is possible for a plurality of measuring probes charged with different electrolytes to be kept in an operable state and these functional units to be interchanged quickly.

Prior to a functional unit being decoupled, the pump drive is expediently controlled in such a way that the first pump chamber is expanded to its maximum volume, at least a major portion of the electrolyte fluid thus being drawn into the reservoir chamber. The refinement according to claim 2 then ensures that this state is achieved even if the reversing pump device is carelessly separated from the pump drive before said end position has been completely achieved.

The system is usable if air is applied, at positive or negative pressure relative to ambient air, via the first hose connection only, and the second hose connection is open to ambient air. Compared with such an open system, a closed system in accordance with claim 3 has a number of advantages. Firstly, the electrolyte movement during the measurement becomes more intensive, owing to bilateral antiphase pulling and pushing, as it were, as a result of which the exchange of spent electrolyte at the measuring point, as well as the removal of gas bubbles formed there during electrolysis, is stepped up. Smaller measuring points can be provided, since masking by gas bubbles is reduced, and the measurement can be carried out more rapidly. A further advantage is that, although variable pressures are used in the closed system, these are always kept below atmospheric pressure, at least during the measurement. Should the measuring probe then be lifted off prematurely from the measurement object, owing to carelessness, the atmospheric excess pressure prevents electrolyte fluid from splashing out of the outlet orifice and thus causing damage or even injury.

In accordance with the refinement according to claim 4, the separability from the pump drive can be achieved in a constructionally simple manner.

The development according to claim 5 has the advantage that slow (stepwise) movements can be generated without a transmission, and a stepping motor is available as an inexpensive mass-produced article. Control, too, is simpler.

In accordance with the refinement according to claim 6, guidance and mounting are simple and clear.

The design according to claim 7 simplifies the bearing arrangement of the piston and sealing of the pump chambers. Thus, in particular, sealing of the pump chamber at the piston side can be designed to be completely airtight, without at the same time causing major frictional losses in the sealing area.

The use of an interchangeable functional unit of measuring probe and reversing pump device. By providing measuring probes charged with the electrolyte matching the particular measurement task it is possible to carry out very rapid successive measurements on one measurement object. In so doing, the risk is reduced of the position of the measurement object being changed inadvertently, which would require time-consuming realignment. The contingency of chemical changes on the layers which have been exposed during the previous measurement taking place during the change over to the new measurement likewise is virtually precluded as a result. Not expanding the first pump chamber to its maximum volume during initial charging maintains a margin of safety which ensures that, at the end of a measurement, the electrolyte is drawn essentially completely into the reservoir chamber. The first travel for initiating the measurement is dimensioned in such a way that a sufficient amount of electrolyte reaches the measuring point. During the measurement, the electrolyte is kept in slightly pulsating motion, which ensures that the measuring point is surrounded by flowing active electrolyte, in order thus to shorten the measurement operation.

Further advantageous refinements and developments of the invention will become apparent from the following description of an illustrative embodiment shown in the drawing, in which:

FIG. 1 shows an appliance in accordance with the invention.

The appliance comprises a measuring probe 11, a reversing pump device 12 and a support device 13, here shown only fragmentarily. The latter is designed, in a manner not shown in detail here, for holding a measurement object and for guiding the measuring probe 11 in a movable manner with respect to the measurement object. Additionally, it contains a pump drive 14, including a controller.

The measuring probe 11 is of a design known per se, having essentially two housing sections 15 and 16 slipped onto one another, and has a measuring chamber 17, situated at the bottom in the operating position, and a reservoir chamber 19 which is situated above it and communicates therewith via a cathode pipe 18. At the lowest point of the measuring chamber 17 there is an outlet orifice 21 which is delimited by an annular seal 22. The outlet orifice 21 can therefore be placed onto a measurement object in a liquid-tight manner. The lower mouth of the cathode pipe 18 is situated just above the outlet orifice 21. The cathode pipe 18 is connected to an electrical connection 23 which runs to the measuring electronics. At the highest point of the reservoir chamber 19 there is a first hose connection 24, and at the highest point of the measuring chamber 17 there is a second hose connection 25.

The reversing pump device 12 comprises a pump casing 26, consisting of a central cylinder section 27 having a cylinder bore 28 and cylinder heads 29, 31 fitted on the end sides, and a piston 32 guided in the cylinder bore 28. Formed in the cylinder head 29, coaxially with the cylinder bore 28, is a first pump chamber 33 which is sealed towards the cylinder bore 28 by means of a diaphragm 34 in an airtight manner, but so that its volume is variable. The outer circumferential zone of the diaphragm 34 is clamped between cylinder section 27 and cylinder head 29, while in the central zone the left-hand end of the piston 32 is clipped on. The first pump chamber 33 has a third hose connection 35 which leads to the outside and, via a flexible air line 36, is connected to the first hose connection 24 of the measuring probe 11. Formed in the cylinder head 31, coaxially with the cylinder bore 28, in a symmetrically identical design, is a second pump chamber 37 which is sealed towards the cylinder bore 28 by means of a diaphragm 38 in an airtight manner, but so that its volume is variable. The outer circumferential zone of the diaphragm 38 is clamped between cylinder section 27 and cylinder head 31, while in the central zone the right-hand end of the piston 32 is clipped on. The second pump chamber 37 has a fourth hose connection 39 which leads to the outside and, via a flexible air line 41, is connected to the second hose connection 25 of the measuring probe 11.

The cylinder section 27 has, approximately in the centre an insertion orifice 42 which opens radially into the cylinder bore 28 and through which an eccentric shaft 43 can be inserted. In the process, the latter dips into an edge recess 44 of the piston 32, which edge recess 44 forms a radial coupling surface 45 towards the side of the cylinder head 29. Opposite it, a further coupling surface 46 may also be formed. The eccentric shaft 43 is attached eccentrically to a motor shaft 47 which forms part of a stepping motor 48. In the position as drawn, the piston 32 is in its median position between the cylinder heads 29, 31, so that the eccentricity of the eccentric shaft 43 with respect to the motor shaft 47 is not visible. Disposed on the inner end of the eccentric shaft 43 there is preferably a ball race 49 which with its circumference fits with little play between the parallel coupling surfaces 45, 46.

The stepping motor 48 is supported, in a manner not shown in detail, in a support housing 51 forming part of the support device 13, so that the eccentric shaft 43 projects beyond the outside 52 thereof. Vertically projecting from the said outside 52 are also two guide pins 53, 54 which engage in corresponding holes in the cylinder heads 29, 31 and thus hold the reversing pump device 12 on the support housing 51 in a detachable manner. It goes without saying that the guide pins 53, 54 can also be arranged in other spatial positions relative to the reversing pump device 12.

The cylinder bore 28 has, adjacent to the diaphragm 34, a ledge 55 which projects radially inwards and which supports one end of a compression spring 56 whose other end rests against a thrust ring surface 57 of the piston 32. Said compression spring 56 causes the piston 32, in the event that the eccentric shaft 43 is not inserted into the edge recess 44, to be pushed so far to the right that the first pump chamber 33 is expanded to its operationally maximal volume.

In the region of the outside 52, a detector (microswitch) (not shown in detail) is provided which reports the presence of a reversing pump device 12 and, when such a device is removed, causes the controller of the stepping motor 48 to move the eccentric shaft 43 into that position into which the edge recess 44 in the piston 32 is displaced owing to the spring action. This ensures that a reversing pump device can be slipped on without difficulty.

The operational procedure of the appliance divides into the initial charging of the measuring probe 11, the preparation for the measurement, the performance of the measurement, and the completion of the measurement. This can finally be followed by the step of emptying the measuring probe 11 if the electrolyte is spent or the measuring probe will not be used for some time.

For the purpose of initial charging, the reversing pump device 12 is coupled with the pump drive 14, whereupon the first pump chamber 33 is compressed to its minimum volume, followed by the lower housing section 15 of the measuring probe 11 being detached and the cathode pipe 18 being immersed into a vessel containing the desired electrolyte fluid. The stepping motor 48 is then driven with such a number of rotary steps that the first pump chamber 33 is expanded to approximately 70% of its maximum volume. As a result, electrolyte is drawn into the reservoir chamber 19, but does not pass into the air line 36. Then the housing section 15 is slipped back onto the housing section 16, the measuring probe thus being ready for service. The measurement can now be initiated, or the reversing pump device 12 is separated from the support device 13. The compression spring 56 thereupon expands the first pump chamber 33 to its maximum volume. It is then possible to prepare for service, in the manner described above, a plurality of measuring probes of the same type each having different electrolyte fluids.

For the purpose of preparing or initiating a measurement, a charged measuring probe 11 is mounted on the support device 13 so as to be finely adjustable relative to the measurement object, and the reversing pump device 12 linked to the probe as a functional unit is coupled to the pump drive 14. Then the measuring probe 11 is placed by its outlet orifice 21 onto the measuring point of the measurement object and the stepping motor 48 is activated via a feet-switch, for example, so that it carries out a predefined first number of rotary steps under program control, which causes the piston 32 to move towards the first pump chamber 33. The attendant contraction of the first pump chamber 33 forces a corresponding portion of the electrolyte fluid from the reservoir chamber 19 via the cathode pipe 18 into the measuring chamber 17. Now the measurement can start.

During the measurement the stepping motor 48, likewise under program control, is activated in a continuously reciprocating manner alternately with a second number of rotary steps forwards and backwards again in each case, so that the electrolyte fluid present in the measuring chamber 17, particularly in the region of the measuring point, is moved in a pulsating manner. As a result, electrolyte spent at the measuring point is exchanged, and gas bubbles formed during the electrolytic delamination are removed from the measuring point. The second number of rotary steps is smaller for said pulsating pump movement than the first number for charging the measuring chamber 17. The analysis of the measurement is performed in a manner known per se.

For the purpose of terminating the measurement, the stepping motor 48 is moved back into its starting position, so that the first pump chamber 33 is expanded to its maximum volume. This causes the electrolyte present in the measurement chamber 17 to be drawn back into the reservoir chamber 19. The same effect is produced, owing to the compression spring 56, as soon as the reversing pump device 12 is inadvertently separated prematurely from the pump drive 14.

The successive layer thicknesses on a measurement object provided with a plurality of different coatings can be measured quite simply by measuring probes containing the electrolyte appropriate for each case being employed successively. Since interchange can be carried out quickly and without difficulty, the measurement object remains reliably in position, so that the measuring probes can be placed onto the measuring point again and again with high precision and without time-consuming realignment.

To empty a measuring probe 11, the housing section 15 is removed and the cathode pipe 18 is held over a receptacle. The stepping motor 48 is then allowed to run continuously for some time, so that the piston executes its full travel a number of times. As a result, the contents of the reservoir chamber 19 are ejected.

The above description shows that what matters is primarily the first pump chamber 33 with its pumping effect on the reservoir chamber 19. Indeed, a simplified design can be reduced to this. The second pump chamber 37 which acts in push-pull or in antiphase on the measuring chamber 17 has advantages which have been pointed out in the introduction. As an alternative to the two pump chambers combined constructionally into a reversing pump device, it is also possible to provide two separate diaphragm pumps, but these are more complex to handle. The compression spring 56 can be dispensed with if the diaphragms 34, 38 themselves are prestressed. Any prestress can also be dispensed with if the piston runs with a certain stiffness, so that it comes to a halt in the position defined by the pump drive if it is separated therefrom. This does, however, mean doing without the facility of the electrolyte being drawn back in automatically in the event of inadvertent detachment.

I claim:

1. Appliance for the coulometric measurement of the thickness of metallic coatings, comprising a measuring probe, a reversing pump device and a support device for mounting a measurement object, guiding the measuring probe relative to the measurement object and bearing arrangement for a pump drive, the measuring probe having a measuring chamber and a reservoir chamber which communicates therewith via a cathode pipe and has a first hose connection, the measuring chamber having an outlet orifice, which can be placed onto the measurement object, and a second hose connection, and furthermore the reversing pump device having a third hose connection at which positive pressure or negative pressure relative to the pressure prevailing in the region of the second hose connection in the measuring chamber can be generated, and the first and third hose connections, finally, being connected via an air line, characterized in that the measuring probe (11), connected via the air line (36) to the reversing pump device (12), constitutes a functional unit which is designed so as to be readily detachable from the pump drive (14) and the support device (13).

2. Appliance according to claim 1, characterized in that the third hose connection (35) opens into a first pump chamber (33) and in that the reversing pump device (12) has a restoring-spring arrangement (56) which expands the first pump chamber (33) to its operationally maximal volume as soon as the pump drive (14) has been uncoupled.

3. Applicance according to claim 1, characterized in that the second hose connection (25) is connected, via a further air line (41), to a fourth hose connection (39) which opens into a second pump chamber (37), the pump chambers (33, 37) being separate from one another and their volumes being variable in antiphase.

4. Appliance according to claim 3, characterized in that the reversing pump device (12) has a pump casing (26) with a piston (32) which is supported therein in a reciprocatingly movable manner and, with axially opposite ends, delimits both the first and second pump chambers (33, 37) in a volume-varying manner, part of the central region of the piston (32) being fashioned as a coupling surface (45) for an eccentric shaft (43, 49), which eccentric shaft (43) is a component of the pump drive (14) and can be inserted, through an insertion orifice (42) which radially traverses the pump casing (26, 27), into the contact region of the coupling surface (45).

5. Appliance according to claim 4, characterized in that the eccentric shaft (43) can be driven in a rotary manner by a stepping motor (48) which is a component of the pump drive (14), at least 20 rotary steps effecting a 360° turn of the eccentric shaft (43).

6. Appliance according to claim 4, characterized in that the pump drive (14) is arranged in a support housing (51) forming part of the support device (13), the eccentric shaft (43) projecting perpendicularly beyond the outside (52) of the support housing (51), and in that two guide pins (53, 54) project perpendicularly from the outside (52), it being possible for at least subregions of the pump casing (26) to be pushed in, in between the guide pins (53, 54).

7. Appliance according to claim 4, characterized in that the first and second pump chambers (33, 37) are sealed in an airtight manner towards the piston (32) by one diaphragm (34, 38) each, onto which the opposite ends of the piston (32) are clipped.

* * * * *